（12）United States Patent
Hasei et al.

(10) Patent No.: US 6,413,397 B2
(45) Date of Patent: *Jul. 2, 2002

(54) NITROGEN OXIDE GAS SENSOR (75) Inventors: Masaharu Hasei; Yongtie Yan; Akira Kunimoto, all of Kumagaya (JP)

(73) Assignee: Kabushiki Kaisha Riken, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/828,894

(22) Filed: Apr. 10, 2001

Related U.S. Application Data (62) Division of application No. 09/339,108, filed on Jun. 24, 1999, now Pat. No. 6,274,016.

(30) Foreign Application Priority Data

Jun. 29, 1998 (JP) .......................................... 10-182336

(51) Int. Cl.[7] .............................................. G01N 27/407
(52) U.S. Cl. ........................ 204/424; 204/425; 204/426; 204/427; 204/291; 204/292; 204/293; 205/781
(58) Field of Search ............................... 204/424–429, 204/291–293

(56) References Cited

U.S. PATENT DOCUMENTS

| | | | |
|---|---|---|---|
| 3,843,400 A | 10/1974 | Radford et al. | 204/429 |
| 4,199,425 A | 4/1980 | Sinkevitch | 204/195 |
| 4,207,159 A | 6/1980 | Kimura et al. | 204/426 |
| 4,395,319 A * | 7/1983 | Torisu et al. | |
| 4,595,485 A * | 6/1986 | Takahashi et al. | |
| 4,927,517 A * | 5/1990 | Mizutani et al. | |
| 5,672,811 A | 9/1997 | Kato et al. | 204/426 |
| 6,274,016 B1 * | 8/2001 | Hasei et al. | |

FOREIGN PATENT DOCUMENTS

| | | |
|---|---|---|
| EP | 0 331 050 A | 9/1989 |
| JP | 59-91358 | 5/1984 |
| JP | 07-198671 | 8/1995 |
| JP | 08-43346 | 2/1996 |
| JP | 08-271476 | 10/1996 |

* cited by examiner

*Primary Examiner*—T. Tung
(74) *Attorney, Agent, or Firm*—Kubovcik & Kubovcik (57) ABSTRACT

A nitrogen oxide gas sensor wherein an alloy electrode of platinum and rhodium or a cermet electrode of platinum, rhodium, and zirconia or of a rhodium alloy and zirconia is used as the gas sensing electrode. The electrode of the sensor is suitable for measuring nitrogen oxide such as NO and $NO_2$ in an exhaust gas.

11 Claims, 10 Drawing Sheets

NITROGEN OXIDE GAS SENSOR

This application is a divisional of U.S. patent application. Ser. No. 09/339,108, filed Jun. 24, 1999, now U.S. Pat. No. 6,274,016.

BACKGROUND OF THE INVENTION

The present invention relates to a solid type sensor for a nitrogen oxide gas, and more specifically to a nitrogen oxide gas sensor suitable for measuring $NO_x$ discharged from general combustion system and $NO_x$ in indoor environments, and particularly for sensing $NO_x$ in the exhaust gas of automobiles, where the gas temperature may reach quite high degree.

A gas sensor of the system of forming a sensing electrode and a counter electrode thereof on a zirconia solid electrolyte substrate and sensing the concentration of $NO_x$ by measuring the potential difference between the electrodes has already been reported. For example, gas sensors described in Japanese Patent Laid-Open Publication No. Hei 7-198671 and Japanese Patent Laid-Open Publication No. Hei 8-43346 each has a construction that a sensing electrode made up of a metal oxide such as $CdMn_2O_4$ or $NiCr_2O_4$ and a Pt counter electrode are formed on a zirconia solid electrolyte substrate as an oxygen ion conductor and it can be said, therefore, that these gas sensors have a heat resistance capable of being used in a high-temperature atmosphere.

On the other hand, as a sensing electrode having a sufficient heat resistance in a high-temperature atmosphere such as in an exhaust gas of automobiles, etc., even a noble metal electrode can be expected to be used. In this point, a Pt electrode has been already used as an electrode in a λ oxygen sensor of automobiles and a linear air-fuel oxygen sensor and the high reliance in the practically used has been already proved. The noble metal electrode has many merits of a chemical stability thereof, the easiness of the preparation thereof, capability of expecting the reduction of the impedance of the electrode, etc. The examples of the sensor relating to a $NO_x$ gas using a noble metal sensing electrode on a zirconia solid electrolyte substrate cited in Japanese Patent Laid-Open Publication No. Hei 8-271476 are as follows.

One of them is disclosed in U.S. Pat. No. 4,199,425, which illustrates a sensor prepared by forming an alumina overcoat layer impregnated with Rh for imparting a $NO_x$ sensing to a concentration-cell type oxygen sensor (λ sensor) for automobiles. However, in this sensor structure, the role of the overcoat layer impregnated with Rh is a $NO_x$ decomposition catalyst layer and it is clear that oxygen itself formed by the decomposition of $NO_x$ is sensed by the Pt sensing electrode.

Another one is shown in Japanese Patent Laid-Open Publication No. Sho 59-91358, which discloses a sensor prepared by forming an electrode made up of a noble metal such as Pt, Rh, Pd, Au, etc., and a sensing electrode prepared by laminating or applying an $N_2O$ decomposition catalyst such as $Co_3O_4$ on the above-described electrode on a zirconia solid electrolyte substrate, and in which the potential difference between the electrodes is measured. However, in the case of measuring $NO_x$ in the exhaust gas from automobile engines, the target gases are NO and $NO_2$ and thus by the sensor for $N_2O$, the sum of NO and $NO_2$ gases cannot be measured. Furthermore, the potential difference as sensor outputs to a low-concentration gas is very small and in the middle concentration range (several 1000 ppm or lower) of the real exhaust gas, the potential difference is almost same as zero.

As described above, although a noble metal sensing electrode is used in a concentration-cell type $NO_x$ sensor, the role thereof is simply as a $NO_x$ decomposition catalyst or only functions as a current collector of collecting electron charges generated in the decomposition reaction by the catalyst layer. Furthermore, as mentioned in Japanese Patent Laid-Open Publication No. Hei 8-271476, it is the present state that in the $NO_x$ sensor using a conventional noble metal sensing electrode, the potential difference as sensor outputs is small, the dependence on the oxygen concentration in a detection gas atmosphere is strong, and further the sensor can only be operated and sensing with decomposing $NO_x$.

As described above, in the potential difference-type $NO_x$ sensor using an oxide electrode, a high sensitivity is obtained but the resistance of the sensing electrode is high and thus a current collector must be formed in the sensing electrode to reduce the electrode area.

On the other hand, in the noble metal electrode which is a good electric conductor as an electrode material, there is no such an electrode which measures the $NO_x$ potential difference as it is. The noble metal electrode can have a little sensitivity only to $N_2O$ (laughing gas). Furthermore, in the case of noble metal electrode, it is necessary to control the $O_2$ concentration correctly because the potential difference depends on oxygen partial pressure.

SUMMARY OF THE INVENTION

In view of these problems, an object of the present invention is to provide a potential difference-type $NO_x$ sensor having a low sensor impedance, using a noble metal electrode having a good electrode conductivity, and having excellent $NO_x$ sensing characteristics. Furthermore, the object of this invention is also to provide a potential difference-type $NO_x$ sensor capable of measuring the $NO_x$ concentration without being influenced by the oxygen partial pressure of an atmosphere even in the case of applying it to exhaust gases sensing, etc., from automobiles.

The present inventors have found that the above-described object can be attained by the present invention as set forth hereinafter.

That is, the present invention provides (1) a nitrogen oxide gas sensor of a system of measuring a potential difference between a sensing electrode formed on a zirconia solid electrolyte substrate which is an oxygen ion conductor and a platinum counter electrode or a platinum reference electrode insensitive to $NO_x$, which makes a pair with said sensing electrode, on the above-described solid electrolyte substrate, wherein an alloy electrode comprising platinum and rhodium or a cermet electrode comprising platinum, rhodium, and zirconia is used as the gas sensing electrode of said sensor, and (2) the nitrogen oxide gas sensor of (1) wherein in the alloy electrode comprising platinum and rhodium or the cermet electrode comprising platinum, rhodium, and zirconia, the sensing electrode containing rhodium at least 0.5% by weight to the sum total of platinum and rhodium is used.

Also, the present invention provides, as a total $NO_x$ sensor by combining the alloy electrode comprising platinum and rhodium or the cermet electrode comprising platinum, rhodium, and zirconia described above and a sensor structure, (3) a nitrogen oxide gas sensor of a system of carrying out a sensing by introducing gas to be sensed into a chamber formed inside the sensor body each composed of a zirconia solid electrolyte which is an oxygen ion conductor and having a structure that said chamber is composed of a 1st chamber having a gas inlet connected to a gas atmosphere to be sensed or a structure of said 1st chamber and a 2nd chamber connected to the 1st chamber, wherein said sensor comprising a pair of electrodes formed in the 1st chamber and the 2nd chamber for oxygen pumping-out or oxygen pumping-in, a means for controlling the oxygen concentration in the 1st chamber or the 2nd chamber, a sensing electrode for $NO_x$ converted into NO or $NO_2$ in said 1st chamber, and a platinum counter electrode to the sensing electrode formed in the chamber where said sensing electrode placed or a platinum counter electrode formed such that it connects to a duct of keeping a standard oxygen concentration putting the zirconia solid electrolyte substrate between said sensing electrode and said counter electrode, and said sensing electrode is composed of the alloy electrode comprising platinum and rhodium or a cermet electrode comprising platinum, rhodium, and zirconia described above, and (4) the nitrogen oxide gas sensor of (3) wherein the sensor has a system that the oxygen concentration in the chamber having formed therein said sensing electrode is controlled such that the $NO_x$ potential difference is generated from the mixed potential to oxygen and $NO_x$ in the sensing electrode. By the nitrogen oxide gas sensor, the oxygen partial pressure dependence, which becomes a noise of the $NO_x$ sensing, can be substantially removed.

Figure 1:
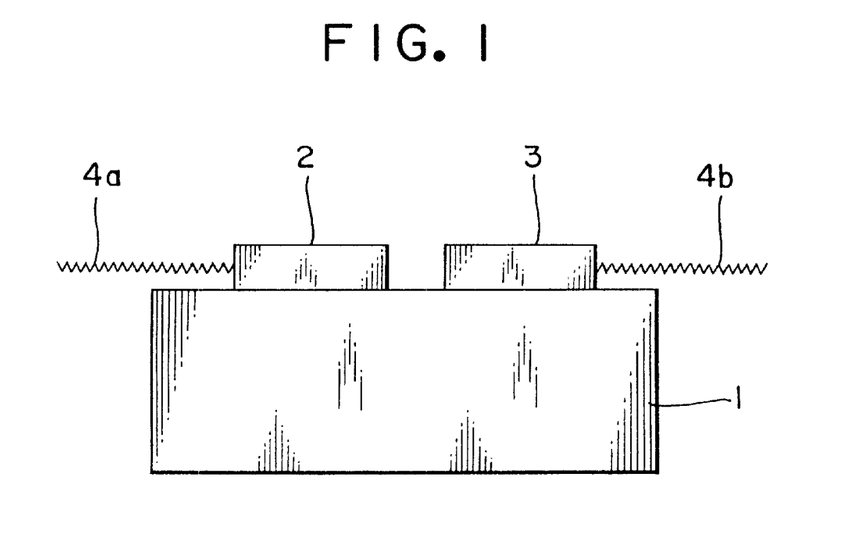
FIG. 1 is a side view showing a fundamental element construction embodiment (disposed on a same surface) of the electrode of this invention.
Figure 2:
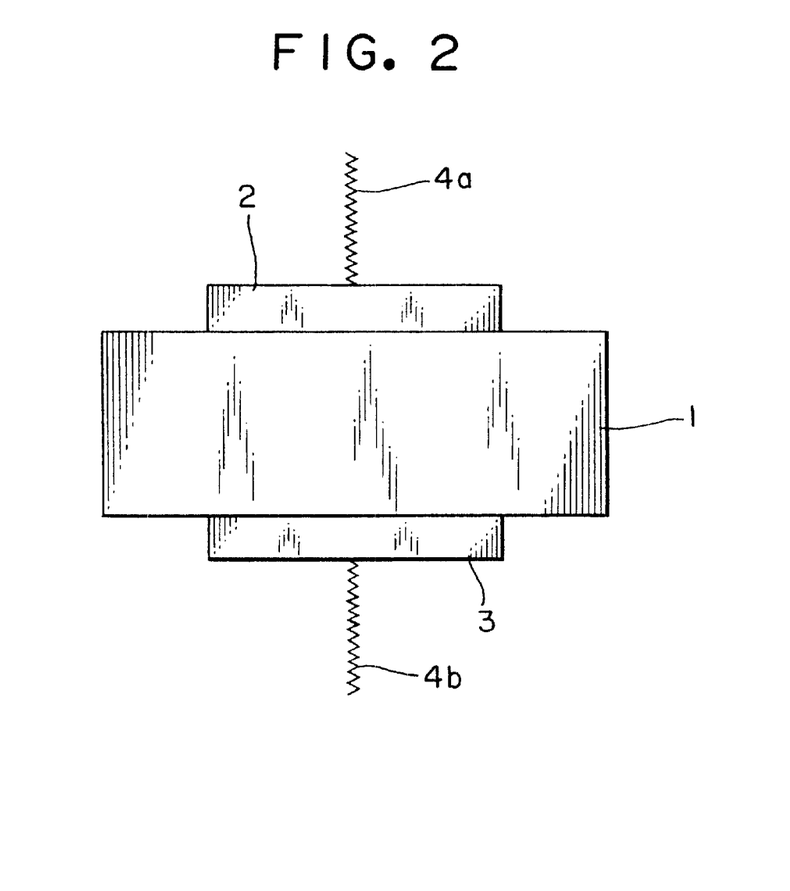
FIG. 2 is a side view of a fundamental element construction embodiment (disposed on the front surface and back surface) of the electrode of this invention.

Explaining in more detail, platinum and rhodium each is used as an $NO_x$ catalyst but the alloy of them has never been used as a potential difference sensing electrode (active to oxygen and $NO_x$) itself. Also, the assertion of the present invention is that the electrode of this invention is used by a different principle from a conventional concentration cell type. That is, the mixed potential [the electrode potential (potential difference to the counter electrode) determined by reactions of $NO_x$ and $O_2$ detection on the sensing electrode] determined by simultaneously taking part in $NO_x$ and oxygen as the oxidation-reduction reaction of $NO_x$ (NO, $NO_2$), is used as an output as the reaction of the $NO_x$ sensing electrode. As the sensor construction, if a sensing electrode 2 and a counter electrode 3 (inactive to $NO_x$) are on a same zirconia solid electrolyte substrate as shown in FIG. 1 and FIG. 2, there is no restriction on the arrangement of them. In this case, however, oxygen must exist in the sensing electrode atmosphere to generate mixed potential. The counter electrode 3 must be inactive to $NO_x$ under the using condition and thus is usually formed of platinum only or formed of platinum added with zirconia for the control of the electrode microstructure.

Figure 3:
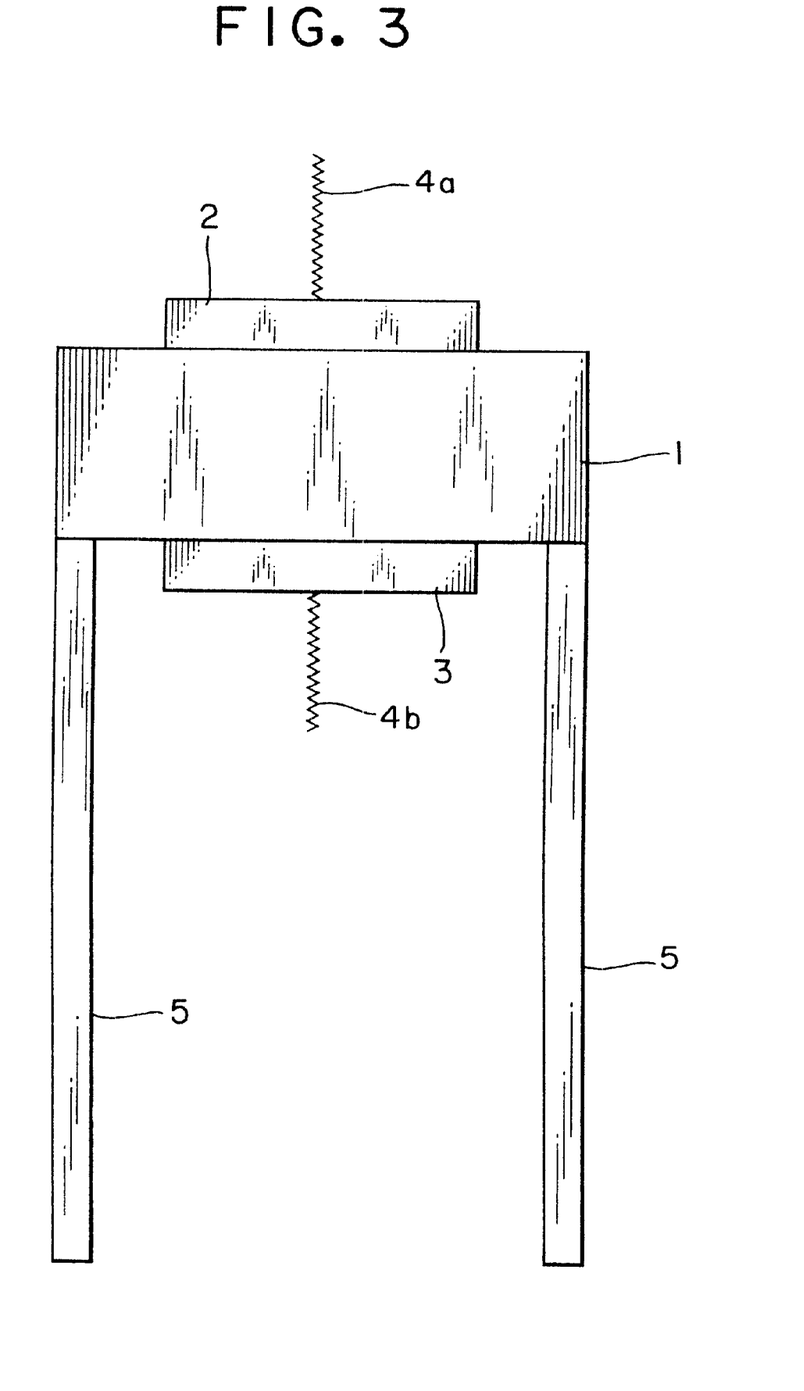
FIG. 3 is a side view showing an application example using the electrode of this invention.

As a matter of course, in the construction shown in FIG. 3, the reference atmosphere at the counter electrode 3 side may be fixed to the air.

Also, when $NO_x$ does not exist in the counter electrode 3 side in the construction shown in FIG. 3, it is clearly in the category of the present invention that the Pt—Rh alloy electrode, etc., for example, of this invention having a sensitivity to $NO_x$ can be used.

In FIG. 1, FIG. 2, and FIGS. 3, 4a and 4b show lead wires from the electrodes 2 and 3 respectively, and 5 shows an isolation walls for isolating the counter electrode 3 from a gas to be sensed.

Under such a condition, in a conventionally reported oxide electrode such as $NiCr_2O_4$, etc., the electric conductivity of the electrode film itself is low and thus it is necessary to form a current collector for catching reaction charges under the electrode. Because the electrode impedance of the oxide electrode itself is large, for example, when it is used for automobile, a noise is liable to occur and it is difficult to ensure the accuracy. Thus, even when it is intended to enlarge the size of the electrode, because of the low electric conductivity of the electrode itself, there occurs a problem that the potential difference can not be measured with good sensitivity without using a current collector.

On the other hand, although a noble metal electrode has a good electric conductivity of electrode, the electrode capable of sensing $NO_x$ as a mixed potential has not yet been found. Hitherto, noble metals used for a $NO_x$ sensor of a potential difference system is from the catalytic property or used as a simple current collector as described above.

The present invention is based on the consideration that by using an alloy film of Pt and Rh for a $NO_x$ sensing electrode, the oxygen adsorption of Pt and the catalysis of Rh are maintained on a same electrode, and the $NO_x$ potential difference by the above-described mixed potential is measured. Accordingly, the dispersion state of Rh (Rh concentration) and the sensitivity of $NO_x$ shall have a co-relation and in fact, such a result has been obtained.

However, the noble metal electrode is active to oxygen itself and when the sensing of a concentration cell type is carried out in, for example, the structure as shown in FIG. 3, the oxygen concentration fluctuation at the sensing electrode 2 side is directly sensed, whereby a precise control of the oxygen partial pressure becomes necessary in the sensing electrode atmosphere. In the region that an oxygen concentration is almost zero, practically, the measurement is carried out by only an oxygen concentration sensor but in this oxygen concentration region, the output dependence on the oxygen concentration is very strong and the precise concentration control is substantially impossible.

On the other hand, in the mixed potential-type sensor which is the application system of the present invention, the oxygen concentration dependence is very weak and even when the oxygen concentration control is substantially very rough, the $NO_x$ output is scarcely influenced. Thus, even in the circumstance which is hitherto considered to be used for automobile, the Pt—Rh alloy electrode of the present system can be practically applied.

Figure 7:
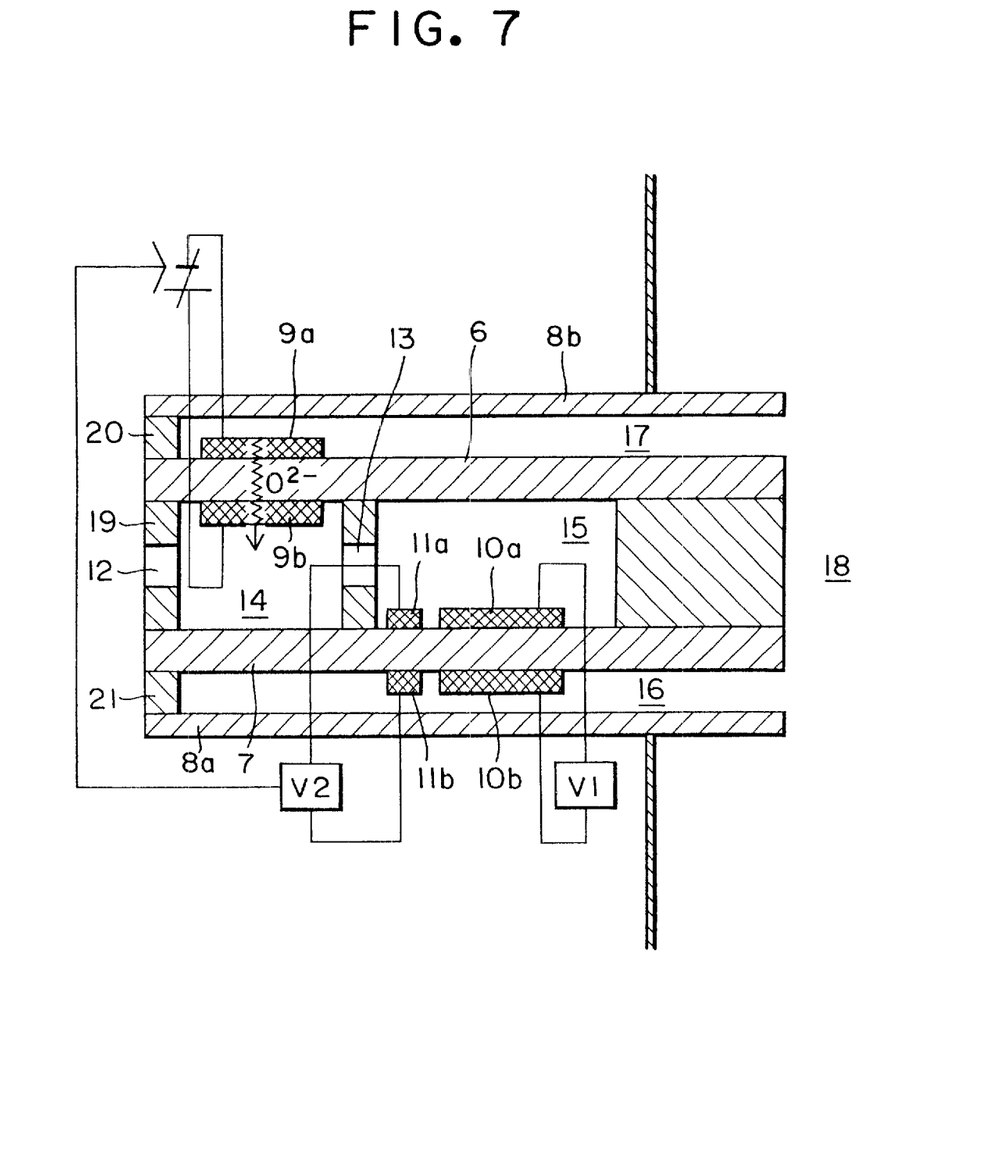
FIG. 7 is a cross-sectional view showing an embodiment of the total $NO_x$ sensor structure to which the electrodes of this invention are applied.
Figure 8:
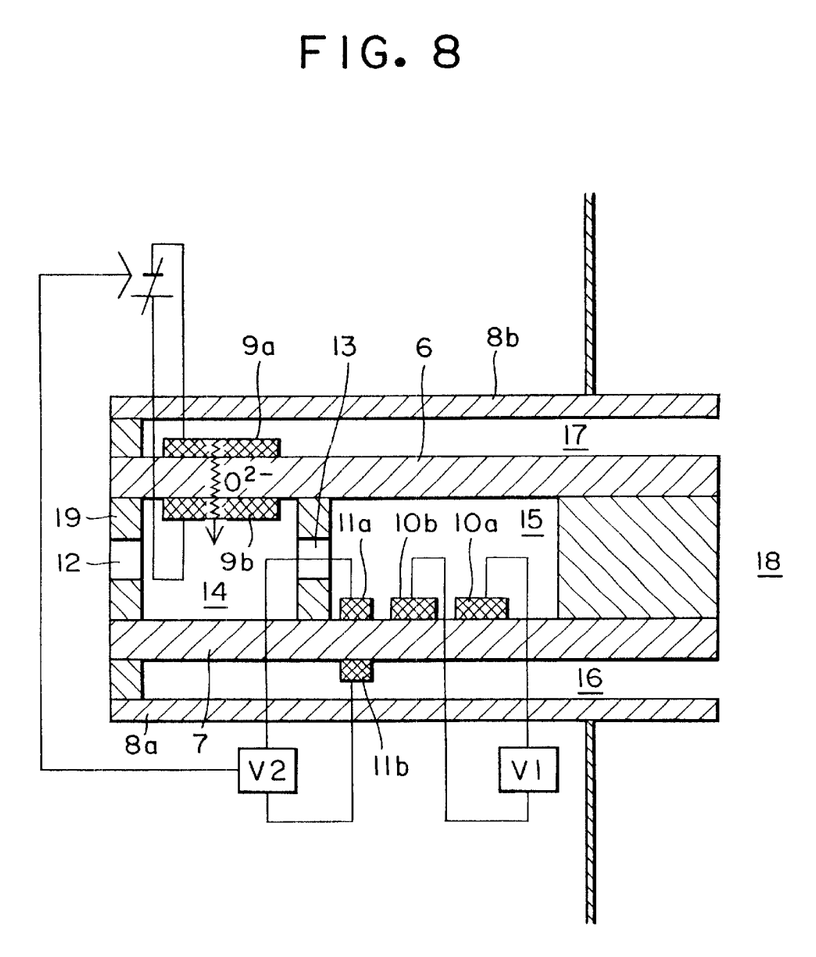
FIG. 8 is a cross-sectional view showing other embodiment of the total $NO_x$ sensor structure to which the electrodes of this invention are applied.

FIG. 7 and FIG. 8 show sensor structures capable of sensing NO or $NO_2$ in exhaust gases of automobiles as total $NO_x$. In a 1st chamber, NO and $NO_2$ in the exhaust gas is simplified into one of NO and $NO_2$ by an oxygen pumping electrode disposed in the same chamber and the potential difference measurement is carried out in the 2nd chamber by the electrode of this invention. That is, in the case of sensing $NO_x$ as $NO_2$, oxygen supply is carried out in the 1st chamber by the pumping electrode and the oxidation of NO is carried out. Conversely, in the case of detecting as NO by the reduction of $NO_2$, the working voltage of the pump is reversed and oxygen is discharged.

In any cases, the oxygen concentration in the 1st chamber is feedback-controlled by the oxygen sensor disposed in the 2nd chamber connected to the 1st chamber. By incorporating the above-described mixed potential sensing system into the sensor structure shown in FIG. 7 or FIG. 8, the oxygen partial pressure dependence of the conventional noble metal electrode itself is largely moderated and the electrode can be applied to a sensor capable of sensing total $NO_x$ as $NO_x$ sensor for automobile.

Moreover, the present invention provides a nitrogen oxide gas sensor of a system of measuring the potential difference between a sensor electrode formed on a zirconia solid electrolyte substrate which is an oxygen ion conductor and a Pt reference electrode without having activity to $NO_x$ on the above-described solid electrolyte substrate, making a pair with said sensing electrode, wherein the gas sensing electrode of said sensor is an electrode formed by laminating a rhodium layer on a platinum layer or a cermet electrode formed by dispersing zirconia in the above-described laminated electrode, and the oxygen concentration of the measuring atmosphere is controlled to a definite value having an optional width of from 0.05 to 21% by volume.

Considering from the circumstance of being used in general rooms to the circumstance of being used in exhaust gases from motorcars, the effects of the present invention are as follows.

In the system of measuring the $NO_x$ concentration by the potential difference, by using the alloy electrode of Pt—Rh, the laminated electrode of Pt and Rh, or the cermet electrode of Pt, Rh, and zirconia each being the electrode in this invention, a very large sensor output, which is never been obtained by conventional noble metal electrodes, is obtained. Thereby, the measurement accuracy of the $NO_x$ concentration is greatly improved.

By using the alloy electrode of Pt—Rh, the laminated electrode of Pt and Rh, or the cermet electrode of Pt, Rh, and zirconia, the electric conductivity of the electrode itself is improved and it becomes unnecessary to form a current collector on a sensing electrode.

In the method of carrying out sintering the electrode with a zirconia green sheet in a body, the problems of the evaporation of the electrode material observed in conventional oxide electrode materials and inferior adhesion do not occur.

Also, by disposing the electrode of this invention in the chamber having an oxygen concentration controlled to a certain extent, the oxygen partial pressure dependence of the electrode itself is removed and the measurement accuracy in practical sensor driving is greatly improved.

DETAILED DESCRIPTION OF THE INVENTION

Then, the present invention is explained in detail.

In this invention, as a zirconia solid electrolyte substrate, a known substrate is utilized.

In this invention, as a formation method of an electrode, a screen printing method is generally used. For the screen printing method, a green sheet can be used as a substrate to be printed. As a matter of course, a sintered substrate can be also used. It is very useful point that a green sheet can be used in this invention. This is because an optional form and a complicated laminated layer structure can be simply formed and also the adhesive property with a cermet electrode can be more increased than the case of using a sintered substrate. However, the present invention is not limited to a green sheet.

Furthermore, the forming method of the electrode in this invention is not limited to the forming method by screen printing and a method of forming a thin film electrode by sputtering, a method of coating a colloid solution, etc., may be used.

In the screen printing method of the present invention, as materials for forming the alloy electrode comprising platinum and rhodium or the cermet electrode comprising platinum, rhodium, and zirconia, a paste prepared by kneading the powders of Pt and Rh or Pt, Rh and $ZrO_2$ with an organic binder such as PVA, etc., and a solvent thereof or a dispersing agent thereof are used. As platinum and rhodium, each powder thereof may be used or a powder of the alloy of them may be used. When a mixed paste of a platinum powder and a rhodium powder is fired at a high temperature of at least 1200° C., they are completely alloyed. This is because firing at a temperature of at least 1300° C. is necessary for sintering a zirconia green sheet.

An addition of zirconia to platinum and rhodium is also carried out by co-precipitating the material powders in the system prepared by directly adding a zirconic acid solution to a Pt-acid solution (same as rhodium solution) at the formation of the material powders.

A material simultaneously adding $Y_2O_3$ to zirconia to impart an ionic conductivity to it is prepared by the same manner as above. The addition of zirconia is also effective for controlling the sintered microstructure of the electrode. The addition amount of zirconia is controlled according to the sintered shrinking amount of a zirconia green sheet and the desired electrode microstructure and is generally from 1 to 20% by weight, and preferably from 5 to 15% by weight for the electrode microstructure.

In the present invention, it is easy to form the platinum-rhodium electrode on the sensor substrate obtained by sintering the laminated zirconia green sheet and it is very effective for improving the $NO_x$ sensitivity. For example, it is effective to use a zirconia sheet with 8 mols of $Y_2O_3$ having a high ionic conductivity as the sensor substrate. In the practical sensor, the addition amount of $Y_2O_3$ in the zirconia green sheet is determined from both the strength characteristics and the long stability of the substrate. That is, the $Y_2O_3$ composition which does not cause a crystal transformation so as to not give a problem to the long stability and exhibits a high strength is desirable.

In the present invention, to prepare the laminated electrode of a platinum layer and a rhodium layer or a cermet electrode obtained by dispersing zirconia to a platinum-rhodium alloy or the above-described electrode, in the case of using a screen printing method, a paste prepared by kneading the material powders for the electrode with an organic binder such as PVA, etc., and a solvent or a dispersing agent thereof, etc., are used. To prepare the laminated electrode described above, first, a Pt film is formed by printing, sputtering, etc. Thereafter, a Rh film is further formed by printing, a vapor deposition method, etc. Particularly, in the case of the vapor-deposited film of Rh, to form a very thin layer, it is necessary to control the film thickness. Also, in the case of forming a Rh layer, by oxidizing the Rh layer, the $NO_x$ sensitivity can be more improved. As a method of forming the oxide layer of Rh, after printing a Rh layer, the Rh layer may be fired in the air, or in the case of forming a Rh layer by a vapor-deposition method, a slight amount of oxygen may be added to the deposition atmosphere.

Also, by further adding a third noble metal to the Pt—Rh electrode, the characteristics can be more improved. For example, by adding Ru, Ir, Pd, Au, or Ag to the Pt—Rh electrode, the gas-responsibility of the electrode can be greatly improved. This is considered to be caused by that the electrode microstructure becomes fine without reducing the $NO_x$ activity of the Pt—Rh electrode. This shows that the electrode impedance is substantially further reduced.

On the other hand, it has been found that iridium, an alloy of iridium and rhodium, or a mixed phase electrode also has a large $NO_x$ activity. Particularly, in an iridium electrode, it becomes a very fine electrode microstructure and the high gas-response speed is obtained. These electrodes are prepared by the same manner of preparing the above-described Pt—Rh electrodes. For example, a paste using an iridium powder is printed on a green sheet and may be fired. Also, a paste is prepared from the alloy powder of iridium and rhodium or a mixture of an iridium powder and a rhodium powder and the electrode is similarly prepared using the paste. However, in this case, it sometimes happens that a part of the Rh phase is separated and precipitated to form a mixed phase.

Apart from this, as the sensing electrode, a mixed phase of platinum and rhodium oxide or an electrode prepared by mixing at least one of the oxides of Ru, Ir, Pd, Ag, Ni, and Cr with the above-described mixed phase may be used.

The oxygen concentration in the measuring atmosphere may be within the range of from 0.5 to 21% by volume. Accordingly, the oxygen concentration is controlled to the range of from 0.5 to 21% by volume.

Then, the present invention is explained by showing the detailed examples.

EXAMPLE 1

Fundamental preparation method and the characteristics in the present invention:

A sensor sample of the structure shown in FIG. 1 was prepared using a green sheet 1 of zirconia added with 8 mols of $Y_2O_3$ as an oxygen ion conductor. The green sheet was prepared by a doctor blade method and had a thickness of 0.3 mm. The green sheet was cut into a sample size of 4 mm×6 mm. As the material for the sensing electrode 2, a paste was prepared by kneading the alloy powder of Pt and Rh with definite amounts of an organic binder and an organic solvent. The addition amount of Rh was 5% by weight to the sum total of Pt and Rh. To control the porosity of the electrode, zirconia was further added to the paste. As a reference electrode 3, Pt paste was printed on the surface of the above-described zirconia sheet 1 such that it made a pair with the sensing electrode 2 and zirconia was dispersed in the reference electrode 3 to control the electrode microstructure, as the case of the sensing electrode 2.

Figure 4:
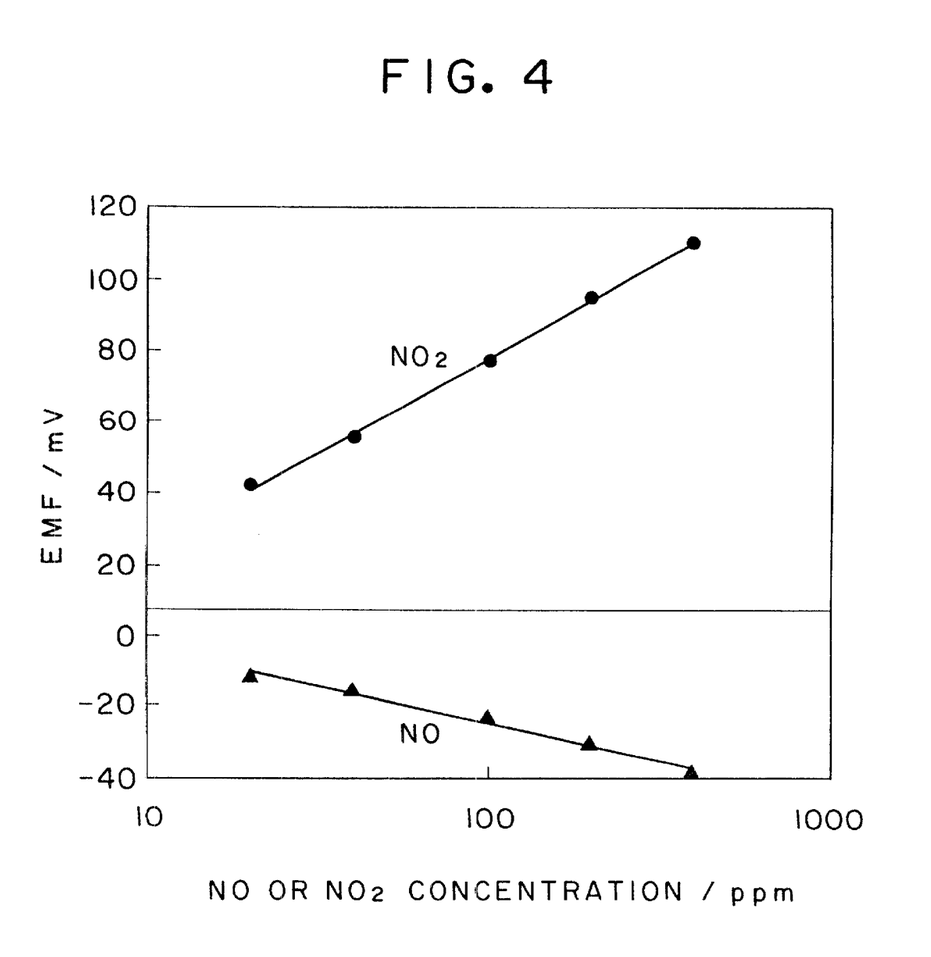
FIG. 4 is a graph showing the element output characteristics ($NO_2$ or NO concentration dependence) of the Pt—Rh (5%) electrode of this invention, wherein EMF represents an electromotive force.

The sample of a green sheet thus prepared was fired at 1400° C. and after connecting Pt lead wires 4a, 4b to the electrodes 2, 3 respectively, the evaluation of NO and $NO_2$ gas sensitivity was carried out. For the gas sensitivity evaluation, a quartz tube was placed in an electric furnace, the sample was inserted in the quartz tube, and while flowing gas to be measured, the potential difference between the sensing electrode 2 and the reference electrode 3 was measured. The gas to be measured was an $N_2$-base gas added with 4% $O_2$ and 50 ppm of NO or $NO_2$ and measurement was carried out at a total flow rate of 5 liters/minute. As the measurement temperature, the temperature of the electric furnace was controlled by a thermocouple placed adjacent to the sensor sample, and the measurement was carried out at an atmospheric temperature of 600° C. FIG. 4 shows the result of the $NO_x$ concentration dependence of the sensor output to $NO_2$ and NO. From the result, it can be seen that the sensitivity to $NO_2$ shows the output of same as or higher than that conventionally reported for $NiCr_2O_4$ sensing electrode. Also, it can be seen that the electrode has a sensitivity to NO.

EXAMPLE 2

Figure 5:
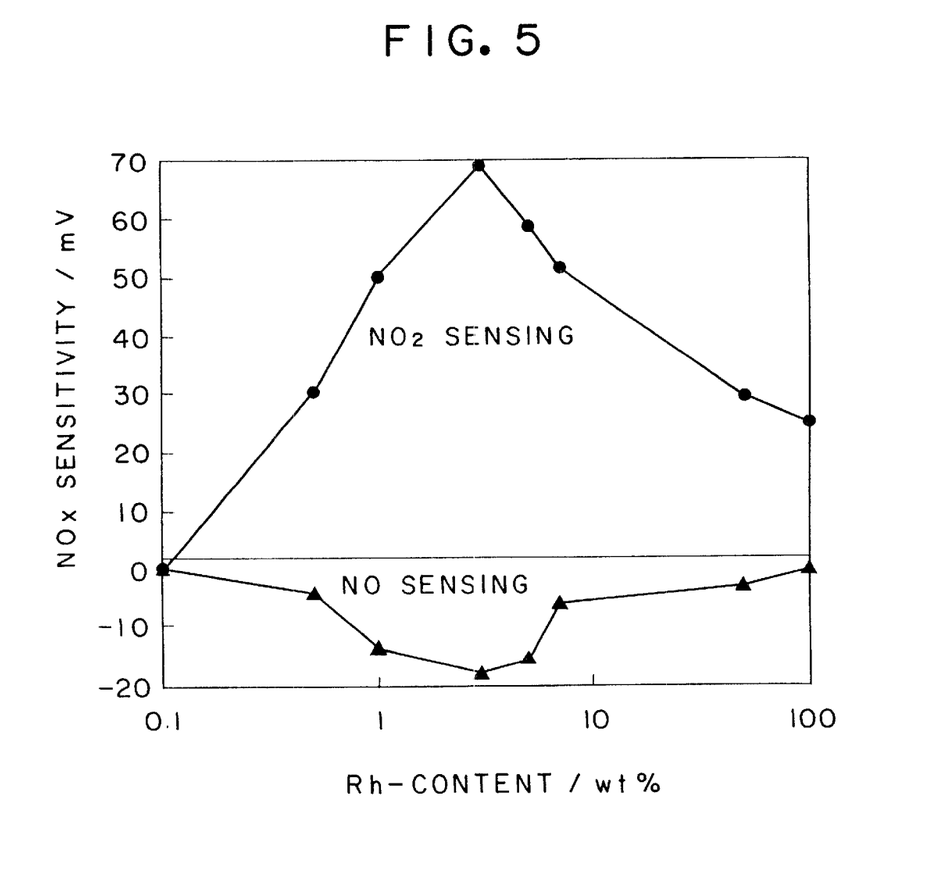
FIG. 5 is a graph showing the Rh composition dependence on the NO, $NO_2$ sensitivity of the electrode of this invention.

Sensor samples each having a changed Rh composition ratio were prepared by the same manner as in Example 1. In this case, however, to control the composition ratio of Pt and Rh, mixed powder of Pt powder and Rh powder was used. The composition ratios of Rh were 0.1%, 0.5%, 1.0%, 3.0%, 5.0%, 7.0%, 50%, and 100% (by weight) to the sum total of Pt and Rh. For the sensitivity measurement, the same apparatus as used in Example 1 was used and the sensitivity to 50 ppm of NO or 50 ppm of $NO_2$ was evaluated at an atmospheric temperature of 600° C. and the total gas flow rate of 5 liters/minute. The results are shown in Table 1 and FIG. 5. From the results, it can be seen that the sensor samples having the Rh composition ratio of 0.5% by weight or higher have a large sensitivity to $NO_2$.

On the other hand, it can be seen that the sensor samples having the Rh composition ratio of from 0.5% to 50% by weight have a sensitivity to NO.

TABLE 1

| Rh Composition ratio | NO Sensitivity | $NO_2$ Sensitivity |
| --- | --- | --- |
| 0.1 wt. % | −0.1 mV | 0.8 mV |
| 0.5 wt. % | −4.3 mV | 30.3 mV |
| 1.0 wt. % | −13.6 mV | 50.2 mV |
| 3.0 wt. % | −17.9 mV | 68.8 mV |
| 5.0 wt. % | −15.4 mV | 58.5 mV |
| 7.0 wt. % | −6.0 mV | 51.5 mV |
| 50 wt. % | −3.0 mV | 29.4 mV |
| 100 wt. % | −0.1 mV | 24.7 mV |

EXAMPLE 3

A sample was prepared almost same as in Example 1 but in this example, the sensor structures shown in FIG. 7 and FIG. 8 respectively were constructed.

Between a substrate 6 of a zirconia solid electrolyte for an oxygen pump and a substrate 7 of a zirconia solid electrolyte for an $NO_x$ sensor and an oxygen sensor, facing each other, is interposed a spacer 19 having a 1st inlet 12 for a gas to be measured and 2nd inlet 13 separated from and opposite to the 1st inlet 12, and a 1st chamber 14 and a 2nd chamber 15 are formed. The substrate 6 has oxygen pump electrodes 9a and 9b on both the surfaces thereof at the 1st chamber 14 side, and the substrate 7 has an $NO_x$ sensing electrode 10a and an $NO_x$ counter electrode 10b thereof, and an oxygen sensing electrode 11a and an oxygen counter electrode 11b, on both the surfaces thereof at the 2nd chamber side. On the other hand, the oxygen pump electrode 9b is exposed in the 1st chamber 14, and the $NO_x$ sensing electrode 10a and the oxygen sensing electrode 11a are exposed in the 2nd chamber 15.

In addition, in the embodiment of FIG. 8, both the $NO_x$ sensing electrode 10a and the $NO_x$ counter electrode 10b are exposed in the 2nd chamber 15 but other construction of the embodiment of FIG. 8 than the above-described point is same as the construction of FIG. 7.

An oxygen-introducing duct partition wall 8b for the $NO_x$ sensor is disposed over the substrate 6 via a spacer 20 facing the substrate to form an oxygen introducing duct 17 for the oxygen pump, and also a standard atmospheric duct partition wall 8a is disposed under the substrate 7 via spacer 21 facing the substrate to form a standard atmospheric duct 16 for the $NO_x$ sensor and the oxygen sensor. Both ducts 16 and 17 are opened to a standard atmosphere (the air) 18.

The potential difference $V_1$ between the $NO_x$ sensing electrode 10a and the $NO_x$ counter electrode 10b and the potential differences $V_2$ between the oxygen sensing electrodes 11a and the counter electrode 11b are measured.

In the sensor structures of the examples of this invention shown in FIG. 7 and FIG. 8, the oxygen concentration in an exhaust gas introduced in the chamber 14 is controlled by the pump electrodes 9a and 9b and $NO_x$ is simplified into NO or $NO_2$. The $NO_x$ simplified into NO or $NO_2$ is sensed as a potential difference by the Pt—Rh (5%) electrodes 10a and Pt electrode 10b in the connected chamber 15. In this case, the oxygen concentration in the chamber 15 is measured by the oxygen sensing electrode 11a and oxygen counter electrode 11b and adjusted to a definite concentration range by the pump electrodes 9a and 9b. By the electrodes 10a and 10b of this invention formed in the chamber 15, NO or $NO_2$ is sensed by a single output $V_1$ of NO or $NO_2$. In the example, the total $NO_x$ output characteristics of a mixed gas of (NO: 25 ppm) and ($NO_2$: 25 ppm) were evaluated in both cases of the $NO_2$ sensing system and the NO sensing system when the oxygen concentration in the chamber 15 is adjusted to the concentration range of from 4% to 50%.

Figure 6:
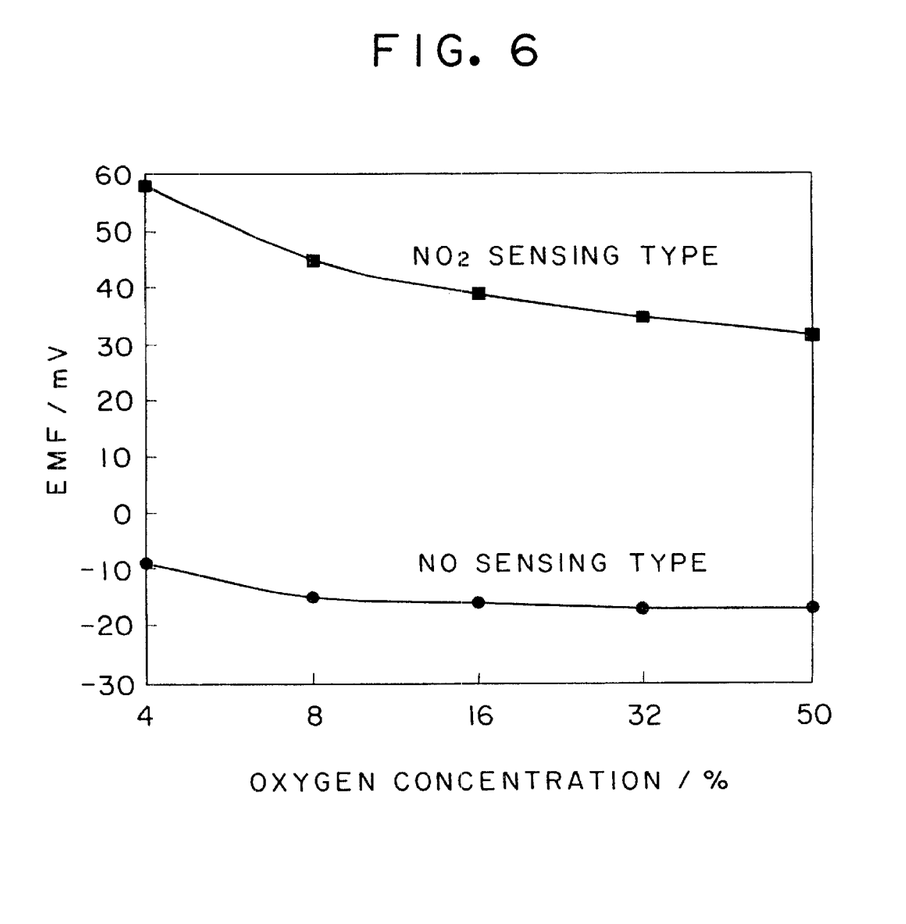
FIG. 6 is a graph showing the controlled oxygen concentration dependence in the total $NO_x$ sensor structure.

As is clear from the results shown in FIG. 6, it can be seen that by applying the electrode of this invention to each of the sensor structures shown in the example, $NO_x$ (NO and $NO_2$) in the exhaust gas is sensed as a total $NO_x$ concentration as well as the strong oxygen concentration dependence of the Pt—Rh sensing electrode itself is removed and a stable $NO_x$ sensing is carried out. That is, in the concentration of oxygen of near 4% which the oxygen concentration dependence is strongest in the measuring range by the $NO_2$ sensing system, even by a rough control of the oxygen concentration of ±1%, the accuracy of ±2.5 ppm can be ensured at a low concentration range sensitivity of $NO_x$: 50 ppm.

On the other hand, it can be seen that in the NO sensing system, the output is almost saturated in the range of high oxygen concentration and when the oxygen concentration is substantially 10% or higher, there is no problem.

EXAMPLE 4

Figure 9:
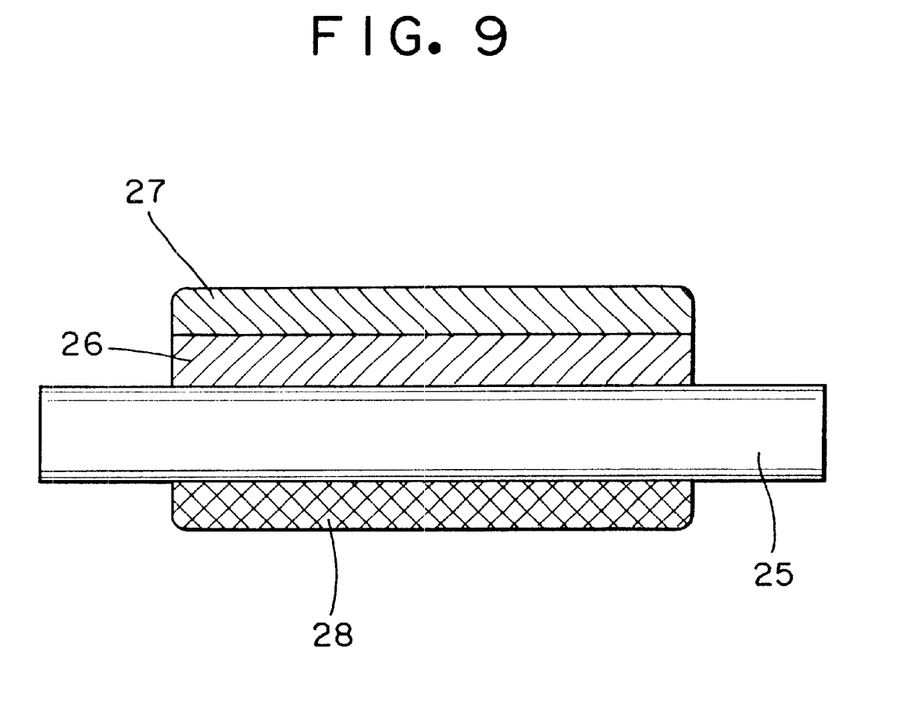
FIG. 9 is a cross-sectional view showing a sensor laminated with Pt and Rh.

As an oxygen ion conductor, a sensor sample of the structure shown in FIG. 9 was prepared using a green sheet of zirconia added with 8 mols of $Y_2O_3$. The green sheet was prepared by a doctor blade method and had a thickness of 0.3 mm. The zirconia green sheet 25 was cut into a sample size of 4 mm×6 mm. Pt paste was prepared by adding a definite amount of an organic binder (for example, PVA) to Pt as a sensing electrode material followed by kneading. Furthermore, Rh paste was prepared by adding a definite amount of an organic binder (for example, PVA) to Rh as a sensing electrode material followed by kneading. First, the Pt paste 26 was formed on the green sheet by screen printing and after drying in an oven, the Rh paste 27 was formed thereon by printing. As a reference electrode 28, the Pt paste was printed on the back surface of the above-described zirconia green sheet 25 so as to make a pair with the sensing electrodes 26 and 27. The sample of a green sheet thus prepared was fired at 1400° C. and after connecting Pt lead wires to the electrodes, the evaluation of the NO and $NO_2$ gas sensitivity was carried out. The Rh film thickness of the sample obtained was about 3 $\mu$m and the Rh film was porous. In the evaluation of the gas sensitivity, a quartz tube was placed in an electric furnace, the sample was inserted in the quartz tube and while flowing gas to be measured, the potential difference between the sensing electrodes 26, 27 and the reference electrode 28 was measured. The gas to be measured was an $N_2$ base gas added with 4% $O_2$ and 300 ppm of NO or $NO_2$ and the measurement was carried out at a total flow rate of 5 liters/minute. As the measurement temperature, the temperature of the electric furnace was controlled by a thermocouple placed adjacent to the sensor sample, and the measurement was carried out at an atmospheric temperature of 600° C. In Table 2, the results of the sensor outputs to $NO_2$ and NO are shown together with the results obtained by using a conventional oxide electrode for comparison. As clear from the results, the sensitivity to $NO_2$ shows the output of same as or higher than that conventionally reported for the $NiCr_2O_4$ sensing electrode. Also, it can be seen that the electrode of this invention also has a sensitivity to NO.

In addition, a sensing electrode prepared by adding zirconia (10% by weight) to each of the pastes described above showed almost the same results as those in Table 2.

TABLE 2

| Sensing electrode | NO 300 ppm | $NO_2$ 300 ppm |
|---|---|---|
| $NiCr_2O_4$ | −25 mV | 97 mV |
| Pt/Rh (Laminated) | −20 mV | 91 mV |

EXAMPLE 5

Figure 10:
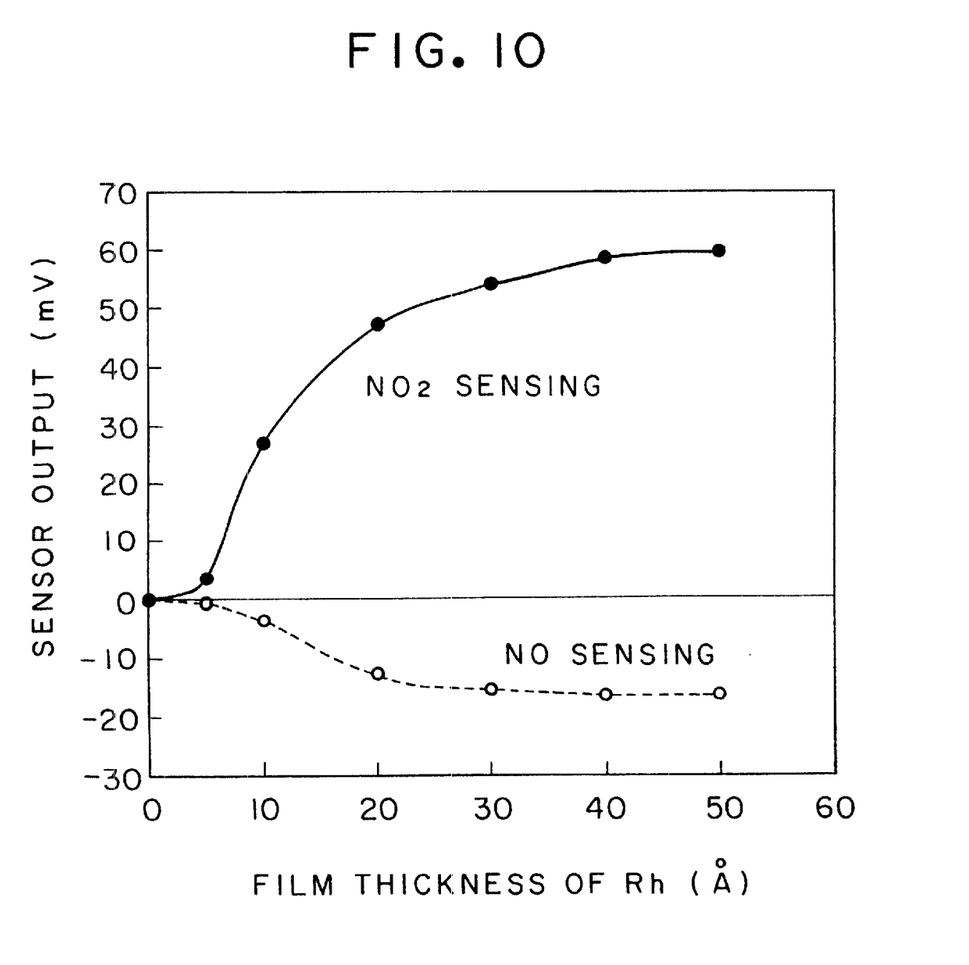
FIG. 10 is a graph showing the sensor output to the Rh film thickness (Å)

A sensor sample was prepared by the same method as in Example 4. In this case, however, as the $NO_x$ sensing electrode, a Pt electrode same as the reference electrode was formed. On the Pt sensing electrode, Rh was deposited by a sputtering method. The relations between the Rh film thickness over-coated, obtained from the relation between the sputtering time and the Rh film thickness, and the 50 ppm NO sensitivity or the 50 ppm $NO_2$ sensitivity are shown in FIG. 10. As is seen from the results, the sensitivity almost tends to be increased from the over-coated film thickness of about 10 angstroms and saturated at the vicinity of 40 angstroms. As described above, it can be seen that a very large sensitivity is obtained by forming the very thin Rh layer.

EXAMPLE 6

Samples were prepared by almost same manner as in Example 4 but in this case, as the sensing electrode materials, Pt—Rh—X was used and as X, each of noble metals, Ru, Ir, Pd, Au, and Ag was added in an amount of from 1 to 10% by weight. About these samples, the $NO_x$ sensitivity was measured as in Example 4.

These results are shown in Table 3. From the results, it can be seen that in each of the samples, the $NO_x$ sensitivity is sufficiently large and the electrode impedance is reduced.

TABLE 3

| Sensing Electrode | NO Sensitivity | $NO_2$ Sensitivity | Electrode Impedance |
|---|---|---|---|
| Pt—Rh(3 wt %) | −12 mV | 102 mV | 232 KΩ |
| Pt—Rh(3 wt %)—Ru(1 wt %) | −26 mV | 111 mV | 44 KΩ |
| Pt—Rh(3 wt %)—Ru(5 wt %) | −19 mV | 100 mV | 37 KΩ |
| Pt—Rh(3 wt %)—Ru(10 wt %) | −13 mV | 81 mV | 22 KΩ |
| Pt—Rh(3 wt %)—Ir(1 wt %) | −7 mV | 48 mV | 49 KΩ |
| Pt—Rh(3 wt %)—Ir(5 wt %) | −14 mV | 78 mV | 73 KΩ |
| Pt—Rh(3 wt %)—Ir(10 wt %) | −21 mV | 97 mV | 102 KΩ |
| Pt—Rh(3 wt %)—Pd(1 wt %) | −11 mV | 69 mV | 87 KΩ |
| Pt—Rh(3 wt %)—Pd(5 wt %) | −9 mV | 54 mV | 40 KΩ |
| Pt—Rh(3 wt %)—Pd(10 wt %) | −5 mV | 36 mV | 34 KΩ |
| Pt—Rh(3 wt %)—Au(1 wt %) | −15 mV | 81 mV | 85 KΩ |
| Pt—Rh(3 wt %)—Au(5 wt %) | −14 mV | 81 mV | 71 KΩ |
| Pt—Rh(3 wt %)—Au(10 wt %) | −11 mV | 72 mV | 66 KΩ |
| Pt—Rh(3 wt %)—Ag(1 wt %) | −19 mV | 91 mV | 60 KΩ |
| Pt—Rh(3 wt %)—Ag(5 wt %) | −6 mV | 57 mV | 288 KΩ |
| Pt—Rh(3 wt %)—Ag(10 wt %) | −3 mV | 36 mV | 150 KΩ |
| Pt—Rh(10 wt %)—Ru(5 wt %) | −16 mV | 72 mV | 96 KΩ |
| Pt—Rh(20 wt %)—Ru(5 wt %) | −10 mV | 47 mV | 88 KΩ |
| Pt—Rh(45 wt %)—Ru(5 wt %) | −6 mV | 34 mV | 133 KΩ |

EXAMPLE 7

After preparing sensor samples as in Example 4, they were subjected to an oxidation treatment at 850° C. In this case, however, as the detection electrode, each of Pt—Rh and Pt—Rh—X (wherein X is Ru, Pd, Ir, Ni, or Cr) was used. The results are shown in Table 4. In the sensing electrodes of the samples obtained, the Rh oxide and the oxide of the third addition element were confirmed by an X-ray diffraction or the surface analysis of XPS. In each case, it can be seen that by applying the oxidation treatment, the sensitivity is largely improved as compared with the electrode before applying the oxidation treatment.

TABLE 4

| Sensing Electrode Material | Before oxidation treatment $NO_2$ Sensitivity | After oxidation treatment $NO_2$ Sensitivity |
|---|---|---|
| Pt—Rh(5 wt %) | 59 mV | 102 mV |
| Pt—Rh(5 wt %)—Ru(5 wt %) | 56 mV | 100 mV |
| Pt—Rh(5 wt %)—Ir(5 wt %) | 46 mV | 75 mV |
| Pt—Rh(5 wt %)—Pd(5 wt %) | 34 mV | 54 mV |
| Pt—Rh(5 wt %)—Ag(5 wt %) | 52 mV | 88 mV |
| Pt—Rh(5 wt %)—NiO(5 wt %) | 61 mV | 85 mV |
| Pt—Rh(5 wt %)—$Cr_2O_3$(5 wt %) | 65 mV | 93 mV |

EXAMPLE 8

Sensor samples were prepared as in Example 1. As the sensing electrodes in the example, an Ir electrode and Ir—Rh alloy electrodes were used. The results of the sensitivity measurement of them are shown in Table 5. From the results, it can be seen that sufficiently large $NO_x$ sensitivity is obtained and also, a good gas-responsibility is obtained.

TABLE 5

| Sensing Electrode Material | 300 ppm NO Sensitivity | 300 ppm $NO_2$ Sensitivity |
|---|---|---|
| Ir | −4 mV | 110 mV |
| Ir—Rh(3 wt %) | −10 mV | 119 mV |
| Ir—Rh(7 wt %) | −9 mV | 115 mV |
| Ir—Rh(10 wt %) | −6 mV | 112 mV |

Figure 11:
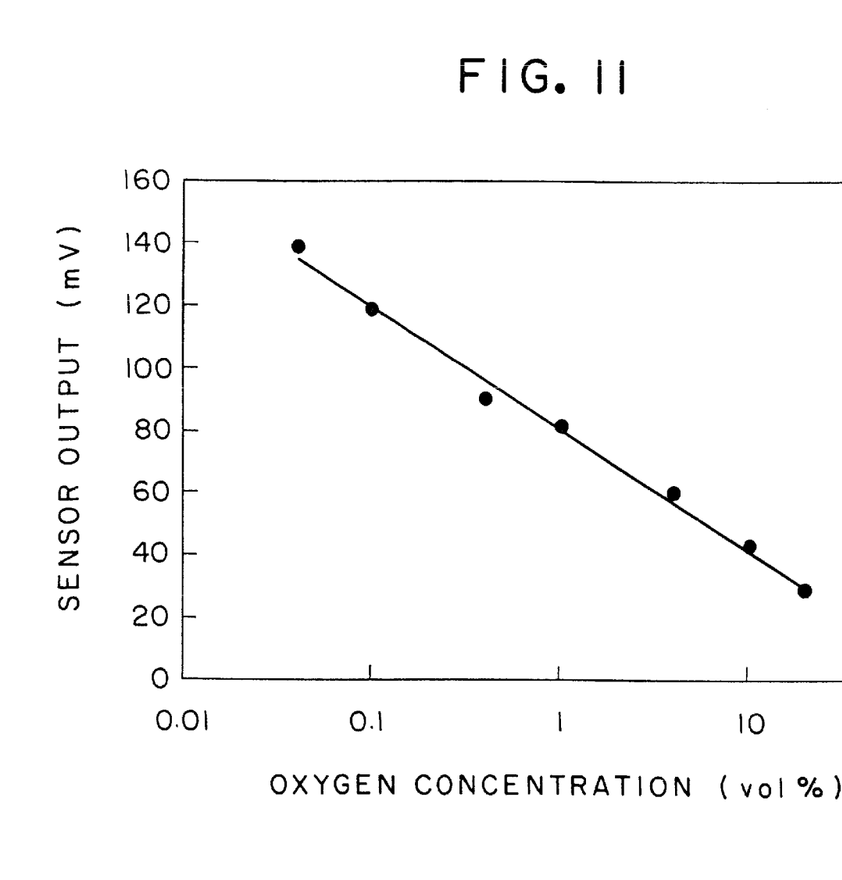
FIG. 11 is a graph showing the sensor output to an oxygen concentration.

In addition, in FIG. 11, the oxygen concentration dependence of an $NO_x$ sensor using a Pt—Rh (3 wt. %) sensing electrode is shown. From FIG. 11, it can be seen that the oxygen concentration should be controlled to a definite value having the range of from 0.05 to 21% by volume.

If the oxygen concentration is lower than 0.05% by volume, the gas-response speed is extremely delayed, which is undesirable. Also, in the chamber structure, the oxygen concentration necessary for removing by oxidation HC and CO in an exhaust gas is preferably from 0.5 to 21% by volume and more preferably from 0.5 to 5% by volume considering the sensor output.

What is claimed is:

1. A nitrogen oxide gas sensor comprising a sensor body; a chamber formed inside the sensor body; a zirconia solid electrolyte substrate which is an oxygen ion conductor forming a wall of said chamber and separating said chamber from an ambient duct; a sensing electrode provided in the chamber on the solid electrolyte substrate, said sensing electrode being an alloy electrode comprising platinum and 0.5–5 wt % rhodium or a cermet electrode comprising zirconia and an alloy of platinum and 0.5–5 wt % rhodium; a platinum counter electrode paired to the sensing electrode, said platinum counter electrode provided in the ambient duct on the solid electrolyte substrate; and means for controlling the oxygen concentration at the sensing electrode.

2. A nitrogen oxide gas sensor of claim 1, wherein the chamber consists of first and second chamber in gas communication with each other, the first chamber is provided with a gas inlet for a gas to be sensed, the means for controlling the oxygen concentration at the sensing electrode is located in the first chamber and the sensing electrode is located in the second chamber.

3. A nitrogen oxide gas sensor of claim 2, wherein the means for controlling the oxygen concentration at the sensing electrode is an oxygen pumping electrode.

4. A nitrogen oxide gas sensor of claim 1, wherein said sensing electrode is an alloy electrode comprising platinum and 2–5 wt % rhodium or a cermet electrode comprising zirconia and an alloy of platinum and 2–5 wt % rhodium.

5. A nitrogen oxide gas sensor comprising a sensor body; a chamber formed inside the sensor body; a zirconia solid electrolyte substrate which is an oxygen ion conductor forming a wall of said chamber and separating said chamber from an ambient duct; a gas sensing electrode provided in the chamber on the solid electrolyte substrate, wherein the gas sensing electrode of said sensor is an electrode formed by laminating a rhodium layer having a thickness of 10–50 Å on a platinum layer or a cermet electrode formed by dispersing zirconia in each of the rhodium layer and the platinum layer of the laminated electrode with a rhodium layer of 10–50 Å thickness; a platinum counter electrode paired to the sensing electrode, said platinum counter electrode provided in the ambient duct on the solid electrolyte substrate; and a means for controlling the oxygen concentration at the sensing electrode in a range of from 0.05 to 21% by volume.

6. A nitrogen oxide gas sensor of claim 5, wherein the rhodium layer of the sensing electrode is deposited by sputtering.

7. A nitrogen oxide gas sensor comprising a sensor body; a chamber formed in side the sensor body; a zirconia solid electrolyte substrate which is an oxygen ion conductor forming a wall of said chamber and separating said chamber from an ambient duct; a gas sensing electrode provided in the chamber on the solid electrolyte substrate, wherein the gas sensing electrode of said gas sensor is made up of an alloy comprising platinum, rhodium and a third metal element, said third metal element being at least one of Ru, Ir, Pd, Au, and Ag; a platinum counter electrode paired to the sensing electrode, said platinum counter electrode provided in the ambient duct on the solid electrolyte substrate; and a means for controlling the oxygen concentration at the sensing electrode in a range of from 0.05 to 21% by volume.

8. A nitrogen oxide gas sensor of claim 7, wherein zirconia is dispersed in said sensing electrode.

9. A nitrogen oxide gas sensor of claim 7, wherein the (Rh + third element)/(Pt + Rh + third element) ratio is from 0.01 to 0.5.

10. A nitrogen oxide gas sensor comprising a sensor body; a chamber formed inside the sensor body; a zirconia solid electrolyte substrate which is an oxygen ion conductor forming a wall of said chamber and separating said chamber from an ambient duct; a gas sensing electrode provided in the chamber on the solid electrolyte substrate, wherein the gas sensing electrode of said gas sensor is made up of a mixed phase rhodium oxide and platinum or an electrode formed by adding at least one of an oxide of a third metal element to a mixture and rhodium oxide and platinum, said third metal element being one of Ru, Ir, Pd, Ag, Ni, and Cr; a platinum counter electrode paired to the sensing electrode, said platinum counter electrode provided in the ambient duct on the solid electrolyte substrate; and a means for controlling the oxygen concentration at the sensing electrode in a range of from 0.05 to 21% by volume.

11. A nitrogen oxide gas sensor comprising a sensor body; a chamber formed inside the sensor body; a zirconia solid electrolyte substrate which is an oxygen ion conductor forming a wall of said chamber and separating said chamber from an ambient duct; a gas sensing electrode provided in the chamber on the solid electrolyte substrate, wherein the gas sensing electrode of said sensor is an electrode comprising iridium, an electrode comprising an alloy or a mixed phase of iridium and rhodium, or a cermet electrode formed by adding zirconia to iridium or an alloy or a mixed phase of iridium and rhodium; a platinum counter electrode paired to the sensing electrode, said platinum counter electrode provided in the ambient duct on the solid electrolyte substrate; and a means for controlling the oxygen concentration at the sensing electrode in a range of from 0.05 to 21% by volume.

* * * * *